United States Patent [19]

Platek

[11] Patent Number: 5,251,496
[45] Date of Patent: Oct. 12, 1993

[54] SURFACE SAMPLING TESTER

[76] Inventor: Gary F. Platek, 9460 Mulberry Rd., Chesterland, Ohio 44026

[21] Appl. No.: 695,685

[22] Filed: May 3, 1991

[51] Int. Cl.⁵ .............................................. G01N 1/14
[52] U.S. Cl. ..................................... 73/864; 134/113
[58] Field of Search ................ 73/864, 864.33, 864.81, 73/864.12, 864.35, 40.7, 38; 134/113, 190; 137/888, 602

[56]  References Cited

U.S. PATENT DOCUMENTS

| | | | |
|---|---|---|---|
| 2,749,149 | 6/1956 | Carpenter | 285/189 |
| 3,762,212 | 10/1973 | Morley et al. | 73/40.7 |
| 4,721,126 | 1/1988 | Horii | 137/888 X |
| 4,864,847 | 9/1989 | Anderson et al. | 73/40.7 |

FOREIGN PATENT DOCUMENTS

| | | | |
|---|---|---|---|
| 825402 | 10/1969 | Canada | 73/864.35 |
| 88639 | 5/1984 | Japan | 73/864.35 |
| 145217 | 10/1961 | U.S.S.R. | 137/888 |

Primary Examiner—Jerry W. Myracle
Attorney, Agent, or Firm—Frederick L. Tolhurst

[57]  ABSTRACT

Apparatus for exposing a rinsing agent to a surface (29) and then collecting the rinsing agent wherein a body (10) defines an internal cavity (12) and wherein a conduit (20) is secured to body (10). Body (10) includes an opening (18) and conduit (20) includes an inlet end (24) that is located in cavity (12) and adjacent to opening (18). A flange (26) is connected to inlet end (24) and cooperates with body (10) and surface (29) to define a chamber (31). The apparatus further includes a gasket (40) that forms a seal between body (10) and surface (29). Rinsing agent that is introduced to cavity (12) passes through chamber (30) and conduit (20) to an outlet end (22).

13 Claims, 3 Drawing Sheets

SURFACE SAMPLING TESTER

BACKGROUND OF THE INVENTION

1. Field of the Invention

The subject invention relates to devices for the collection of analytical samples and, more particularly, devices used in collecting samples of a solvent or rinse agent that is exposed to the surface of an object.

2. Description of the Prior Art

In cleaning impermeable and semi-permeable materials, it is sometimes desirable or even necessary to identify or quantify a contaminant that may be present on the surface of the material. For example, in environmental clean-ups, such a determination is sometimes required to demonstrate that a surface has been adequately cleaned. As a specific example, in cleaning the surface of an object that is contaminated with polychlorinated biphenols ("PCBs"), it is sometimes necessary to demonstrate that the clean-up has achieved a standard that is expressed as an allowable mass of PCB's per unit area of surface.

In the prior art, such samples have sometimes been collected by wiping the material surface with a cloth or other absorbent material. In some instances, the absorbent material is also partially saturated with a rinsing agent or solvent of the contaminant. To demonstrate the amount of contaminant remaining on the surface of the object that is being cleaned, a portion of the cloth is analyzed according to a specified procedure. The amount of contaminant is then attributed to the area that was wiped with the cloth to determine the amount of contamination per unit area. However, this procedure is subject to several uncontrolled variables so that such samples are not always accepted as being representative of the degree of contamination present on the tested surface As an alternative process, a rinsing agent or solvent is sometimes used to determine the degree of contamination that is present on the surface of an object The rinsing agent is exposed to the surface and a sample of the exposed rinsing agent is then analyzed to determine the concentration of contaminant in the rinsate. However, the results of this method are as much subject to the volume of rinsing agent that is used as they are to the amount of contaminant that is present. Moreover, various sample collection devices known in the prior art are not suited for collecting samples of a rinsing agent from the contaminated surface.

An example of such prior art devices is shown in U.S. Pat. No. 3,534,613 to Travor, et al. It describes a device for extracting a sample of the contents of an ordinance or other closed container. According to Travor, a sampling pin is located in a housing that is connected to a detonating assembly. When the detonating assembly is activated, the sampling pin pierces the container surface. The sampling pin is then used to withdraw a sample of the contents of the container. As another example, U.S. Pat. No. 3,521,715 to Kratein describes a device for the collection of soils or other permeable materials. A chemical grout is emitted from a probe when the probe is injected into the semi-permeable material. The grout is allowed to harden and captures a sample of the material when the probe is withdrawn.

Other prior art sample collection devices have merely relied on vacuum or suction techniques and are not suitable for use with a rinsing agent. For example, U.S. Pat. No. 4,088,025 to Foster, et al. and U.S. Pat. No. 3,748,905 to Fletcher, et al. ("Fletcher") describe sampling apparatus wherein vacuum suction is used to collect the sample. Fletcher concerns an apparatus intended to collect air-borne particles at a test surface. A vacuum source draws the particles from the test surface through a tip and a membrane filter housed in a cone assembly. The cone assembly can be inverted and disassembled by mechanical impact to access the filter However, there is no provision for applying a rinsing agent to the surface.

Other apparatus and methods also known in the prior art are subject to various other shortcomings and deficiencies. Thus, there was a need for an apparatus that could be used to expose an area of the surface of an object to a rinsing agent and to collect the rinsing agent for subsequent analysis In addition, there was a need for a device that would define the area of the surface to which the rinsing agent is exposed as well as quantify the amount of rinsing agent that is used.

SUMMARY OF THE INVENTION

In accordance with the subject invention, an apparatus is provided for exposing a rinsing agent to a predetermined area of a surface of an object and then collecting such rinsing agent. The apparatus includes a body that defines an internal cavity. The body also includes at least first and second openings to the cavity. A tube or conduit extends through a portion of the body and is connected to the body such that the outlet end of the tube is located externally from the body and the inlet end of the tube is located inside the body cavity and spaced apart from the second opening to the cavity. A sealing device is located on the external surface of the body adjacent to the periphery of the second opening. When the body is maintained against the surface of the object, a seal is established between the body and the surface of the object such that the body and the sealing device substantially define the area of the surface to which the rinsing agent is exposed.

Preferably, a flange is connected to the inlet end of the tube and is located in the body cavity. The flange includes a surface that is located proximate to and spaced apart from the second body opening. The flange cooperates with the body to define a passageway between the body and the flange.

More preferably, the body is in the general form of a cylinder that includes a foot portion. The foot portion is located at one end of the cylinder adjacent to the second opening.

Still more preferably, the subject invention further includes a plate member that includes a cut-out portion for receiving the body. The plate member cooperates with the body and, preferably, the foot portion thereof for purposes of maintaining the apparatus against the surface of the object.

Other embodiments, objects and advantages of the subject invention will become apparent to those skilled in the art based on the description of the preferred embodiment contained herein.

DESCRIPTION OF THE DRAWINGS

A preferred embodiment of the subject invention is illustrated in the accompanying drawings wherein.

DESCRIPTION OF THE PREFERRED EMBODIMENT

Figure 1:
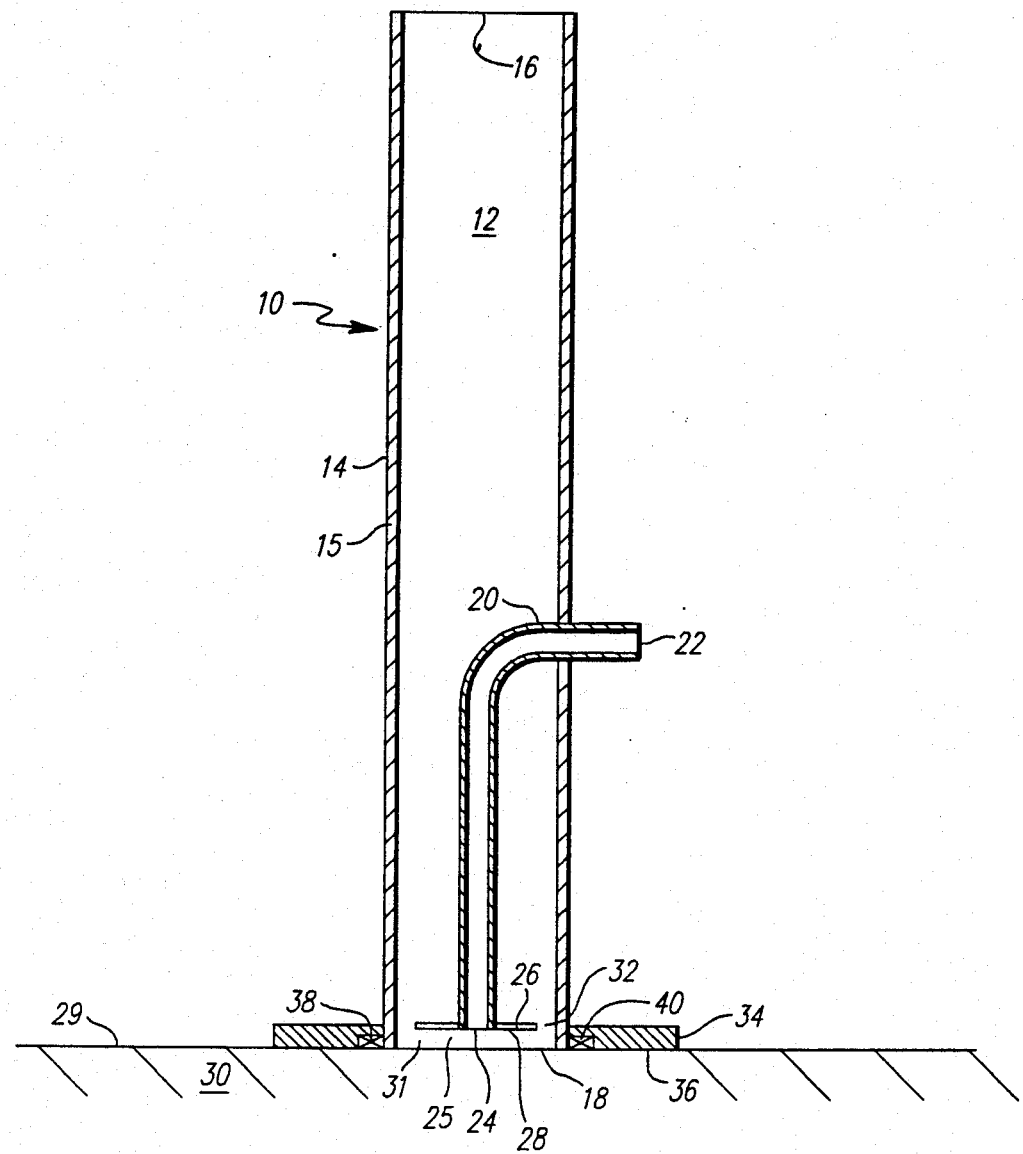
FIG. 1 is an elevational section of the preferred embodiment taken along lines I—I of FIG. 2.
Figure 2:
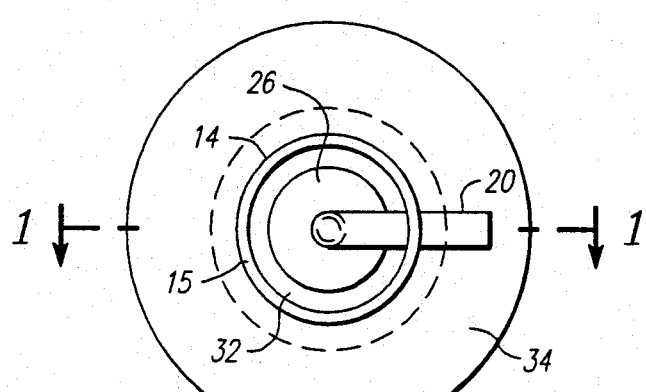
FIG. 2 is a bottom view of the preferred embodiment which shows the sectional view of FIG. 1.

In accordance with the preferred embodiment of the subject invention and as illustrated in the drawings, FIG. 1 shows a sampling apparatus wherein a body 10 defines an internal cavity 12. In FIGS. 1 and 2, body 10 includes a tube that is in the form of a right circular cylinder 14 although other embodiments of body 10 are encompassed within the scope of the subject invention. Cylinder 14 has a wall 15 and includes a first opening 16 that comprises one end of the cylinder 14 and a second opening 18 that comprises the opposite end of cylinder 14. Thus, body 10 defines the perimeter of first opening 16 and the perimeter of second opening 18.

A conduit 20 is connected to cylinder 14 and extends through the wall 15 of cylinder 14 so that a first end or outlet end 22 of conduit 20 is located externally of cylinder 14 and, a second end or inlet end 24 of conduit 20 is located in cavity 12. More particularly, inlet end 24 is located proximate to second opening 18 of cylinder 14 so that inlet end 24 is spaced apart from second opening 18 and inside cavity 12. Preferably, inlet end 24 is spaced in a substantially normal direction from the second opening 18 by a gap 25 or spacing substantially equivalent to less than two-thirds of the square root of the area of second opening 18. More preferably, inlet end 24 is spaced in a substantially normal direction from the second opening 18 by a gap 25 or spacing substantially equivalent to less than one-third of the square root of the area of second opening 18.

A circular flange member 26 is connected to conduit 20 adjacent to inlet end 24 such that conduit 20 passes through the center of flange 26 and flange 26 radially extends from conduit 20. In this way, flange 26 provides a surface 28 that is located proximate to and spaced apart from the second opening 18 of cylinder 14 by a spacing substantially equal to the gap 25 for inlet end 24. As shown in FIG. 1, inlet end 24 of conduit 20 and flange 26 are spaced from second opening 18 such that when cylinder 14 is maintained against a surface 29 of a material 30, a chamber 31 is defined between surface 29, flange 26, and cylinder 14. In addition, flange 26 extends radially from conduit 20 toward cylinder 14. However, flange 26 does not contact cylinder 14 so that a passageway 32 is defined therebetween. Thus, chamber 31 is in communication with the rest of cavity 12 through passageway 32.

Also in accordance with the subject invention, body 10 includes a foot portion 34. Foot 34 is connected to cylinder 14 near the end of cylinder 14 that is adjacent to second opening 18. Foot 34 extends radially from cylinder 14 and includes a surface 36 that substantially coincides with a plane defined by the second opening 18 of cylinder 14. In addition, surface 36 includes a groove or recess 38 for receiving and retaining a sealing means such as a gasket 40. The area of surface 29 that is contacted by rinsing agent is defined by the area circumscribed by the end of body 10 that defines second opening 18 in cooperation with gasket 40. In this way, the area of surface 29 that is contacted by rinsing agent is substantially equal to the area of second opening 18.

In the operation of the preferred embodiment illustrated in FIGS. 1 and 2, the apparatus is placed against the surface 29 of material 30 and urged toward surface 29 such that gasket 40 forms a seal between foot 34 and surface 29. Rinsing agent is then introduced to cavity 12 through the first opening 16 of cylinder 14. The rinsing agent introduced to cavity 12 flows through passageway 32 to chamber 31 where it contacts surface 29. A sufficient quantity of rinsing agent is added to cavity 12 to cause the rinsing agent to flow through conduit 20 to outlet end 22. When surface 29 is substantially horizontal, the level of rinsing agent in cavity 12 and conduit 20 rises until it reaches the portion of conduit 20 that is spaced furthest away from opening 18 in a direction substantially normal to a plane defined by the perimeter of second opening 18. In the preferred embodiment of FIGS. 1 and 2, that level is the level of the outlet end 22 of conduit 20. At that point, the rinsing agent in conduit 20 begins to flow out of outlet end 22 establishing a flow path from cavity 12 through passageway 32, chamber 31 and conduit 20. A predetermined quantity of the rinsing agent is collected from outlet 22 in an appropriate container for analysis. Alternatively, a measured quantity of rinsing agent can be introduced to cavity 12 through first opening 16 such that a predetermined quantity of rinsate will be discharged from outlet end 22 of conduit 20.

In another alternative method of operation, outlet end 22 of conduit 20 is plugged before rinsate is introduced to cavity 12 through first opening 16. In this case, when rinsing agent is introduced through first opening 16, no rinsing agent enters conduit 20 until outlet end 22 of conduit 20 is unplugged. When outlet end 22 is unplugged, rinsing agent will flow through the inlet end 24 of conduit 20 toward outlet end 22. The rinsing agent will flow out of outlet end 22 as long as the level of rinsing agent in cavity 12 is higher than the highest portion of conduit 20, or as long as the pressure in cavity 12 is greater than the ambient pressure at outlet end 22.

Figure 3:
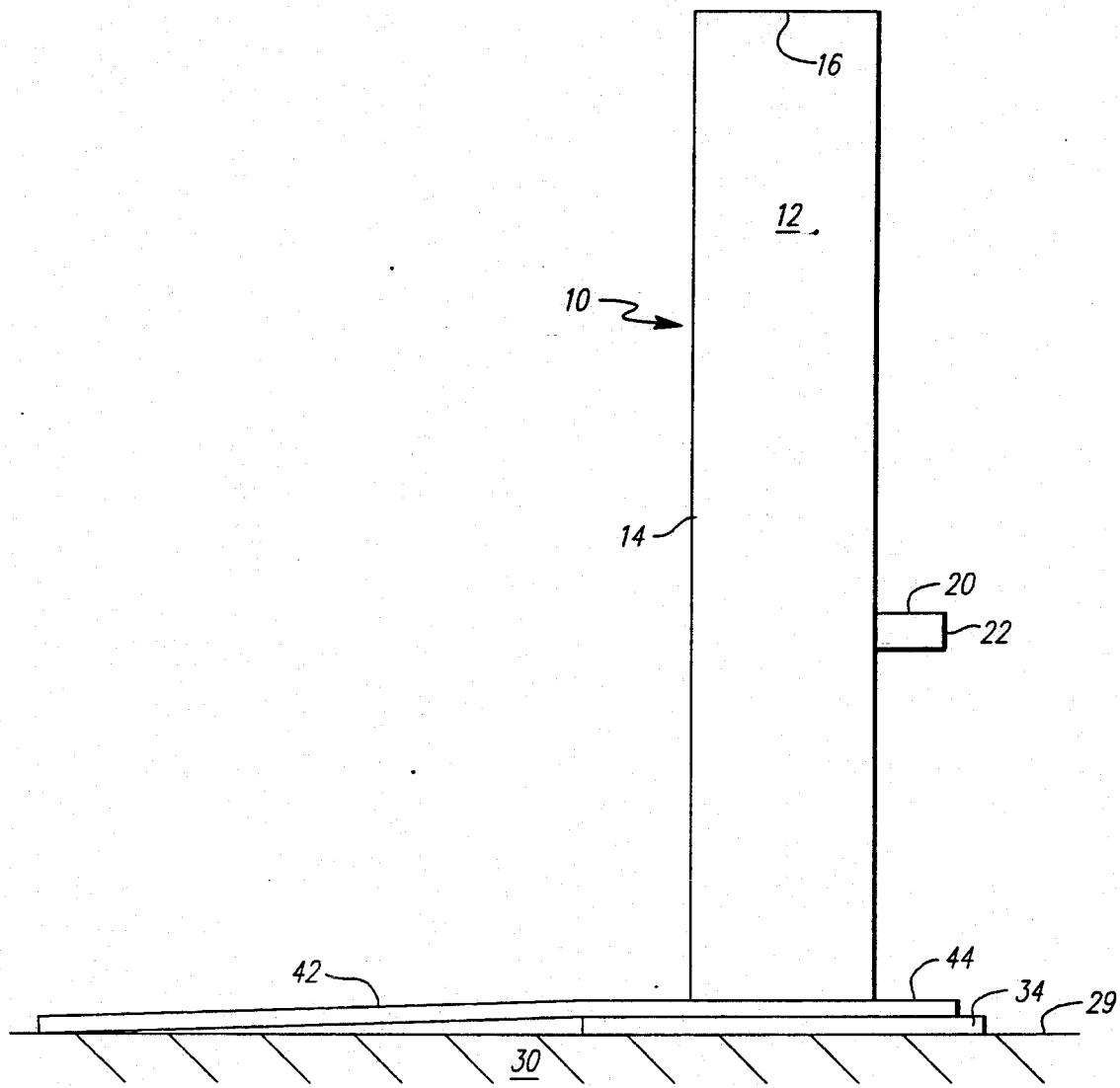
FIG. 3 is an elevation view of the preferred embodiment that includes the plate member as herein described.
Figure 4:
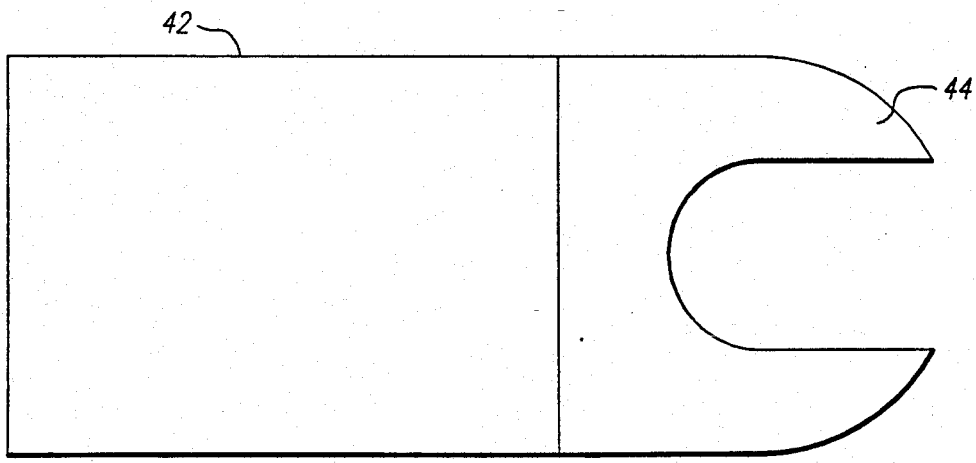
FIG. 4 is a top view of the plate member of FIG. 3 shown in isolation.

As will be appreciated by those skilled in the art, the operation of the invention described with respect to FIGS. 1 and 2 is dependent on the maintenance of a fluid seal between foot 34 and the surface 29 of material 30 by gasket 40. FIGS. 3 and 4 illustrate an alternative embodiment of the subject invention wherein a plate member 42 can be used to increase the pressure on gasket 40, thus improving the reliability of the seal between foot 34 and surface 29. As shown in FIGS. 3 and 4, the plate member 42 includes a cut-out section 44 that is shaped to receive cylinder 14. In the operation of this alternative embodiment, cylinder 14 is placed in cut-out section 44 at a location adjacent to foot 34. Force applied against plate 42 in the direction of material 30 is thus transferred to foot 34 and gasket 40. In this way, the seal between the apparatus of the subject invention and the surface 29 of material 30 is improved.

Figure 5:
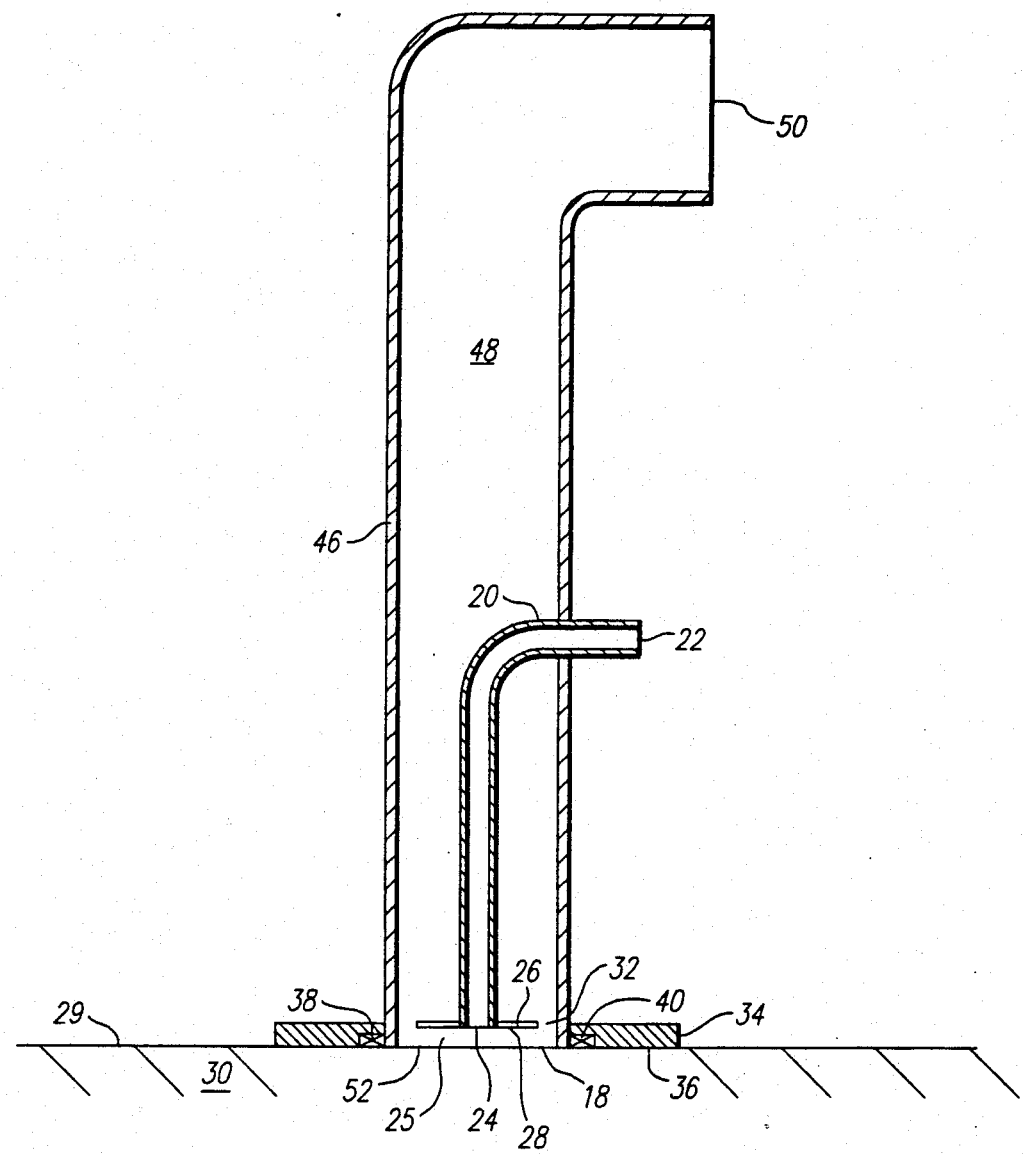
FIG. 5 is an elevation view of an alternative embodiment of the preferred invention.

Another alternative embodiment of the subject invention is illustrated in FIG. 5 wherein like elements are assigned the same reference characters as in FIG. 1. In FIG. 5, a body such as tube 46 is constructed to include a cavity 48, a first opening 50 and a second opening 52. First opening 50 and second opening 52 communicate with cavity 48. As illustrated in FIG. 5, the perimeter of first opening 50 substantially defines a first plane and the perimeter of second opening 52 substantially defines a second plane that intersects or is non-parallel to said first plane. In this way, a sealing means such as gasket 40 can establish a seal on a non-horizontal surface while the first plane defined by the perimeter of first opening 50 is disposed substantially horizontally. Preferably, the perimeter of first opening 50 defines a plane that is disposed substantially orthogonally with respect to the plane defined by the perimeter of second opening 52 so that the alternative embodiment of FIG. 5 can collect rinsing agent from substantially vertical surfaces such as walls.

While a preferred embodiment of the subject invention is described herein in detail, other embodiments, objects and advantages of the subject invention will also be apparent from the description included herein.

I claim:

1. Apparatus for exposing a predetermined area of the surface of an object to a rinsing agent and for collecting such rinsing agent after exposure, said apparatus comprising:
    a body having an internal cavity, said body having at least first and second openings that are in communication with the internal cavity;
    means for supplying the rinsing agent to said internal cavity through said first opening;
    a conduit that is connected to said body, said conduit having a discharge end that is located externally from said body, said conduit also having an inlet end that is located within said internal cavity and spaced apart from the second opening of said body; and
    means for sealing, said sealing means being located adjacent to the second opening of said body and forming a seal between said body and the surface of the object that is to be exposed to the rinsing agent at times when said sealing means is in contact with said surface.

2. Apparatus for exposing a defined area of the surface of an object to a rinsing agent and for collecting the rinsing agent after exposure, said apparatus comprising:
    a body having at least one wall that defines an internal cavity, said body also having at least first and second openings that are in communication with the internal cavity;
    means for supplying the rinsing agent to said internal cavity through said first opening;
    a conduit that is connected to said body, said conduit having a discharge end that it located externally from said body, said conduit also having an inlet end that is located inside said body and spaced apart from the second opening of said body; and
    means for establishing a fluid seal between said body and the surface of the object, said sealing means being located adjacent to the second body opening and forming a seal between said body and the surface of the object at times when said sealing means is in contact with said surface, said sealing means cooperating with said body to define the area of the surface to which the rinsing agent is exposed.

3. The apparatus of claim 2 wherein the wall of said body comprises a substantially circular right cylinder.

4. The apparatus of claim 2 wherein the portion of said body that defines the perimeter of said first opening is substantially in a first plane and the portion of said body that defines the perimeter of said second opening is substantially in a second plane, where said second plane is in substantially non-parallel relationship with respect to the first plane.

5. The apparatus of claims 2, 3 or 4 wherein said body includes a foot portion that is located adjacent to said second opening.

6. The apparatus of claim 2 wherein the inlet end of said conduit is spaced apart from the second opening of said body by a spacing that is less than a length equal to two-thirds of the square root of the area of the second opening.

7. Apparatus for exposing a predetermined area of the surface of an object to a rinsing agent and for collecting such rinsing agent after exposure, said apparatus comprising:
    a body having an internal cavity, said body having at least first and second openings that are in communication with the internal cavity;
    a conduit that is connected to said body, said conduit having a discharge end that is located externally from said body and an inlet end that is located within said internal cavity and adjacent to the second opening of said body;
    a flange that is connected to said conduit adjacent to the inlet end thereof, said flange cooperating with said body to define a passageway between said flange and said body; and
    means for sealing, said sealing means being located adjacent to the second opening of said body and forming a seal between said body and the surface of the object at times when said sealing means is in contact with said surface.

8. Apparatus for exposing a defined area of the surface of an object to a rinsing agent and for collecting such rinsing agent after exposure, said apparatus comprising:
    a body having at least one wall that defines an internal cavity, said body also having at least first and second openings that are in communication with said cavity;
    a conduit that is connected to said body, said conduit having a discharge end that is located externally from said body, said conduit also having an inlet end that is located inside said body and that is spaced apart from the second opening of said body by a spacing that is less than a length equal to two-third of the square root of the area of the second opening of said body;
    a flange that is connected to the inlet end of said conduit, said flange cooperating with said body to define a passageway between said flange and said body; and
    means for sealing between said body and the surface of the object, said sealing means being located adjacent to the second body opening and forming a seal between said body and the surface of the object at times when said sealing means is in contact with said surface and said body is urged toward said surface, said sealing means cooperating with said body to define the area of the surface to which the rinsing agent is exposed.

9. Apparatus for exposing a defined area of the surface of an object to a volume of rinsate and for collecting the rinsate after such exposure, said apparatus comprising:
    a body having an internal cavity, said body also including first and second openings that are in communication with the internal cavity with the periphery of said second opening defining an area that is substantially equal to the area of the surface that is to be exposed to the rinsate;

a conduit that is connected to said body and that extends into said internal cavity, one end of said conduit having an inlet opening that is located within the internal cavity of said body and that is also located adjacent to the second opening of said body, the other end of said conduit having a discharge opening that is located externally from said body;

a flange that is connected to the inlet end of said conduit, said flange being located within the internal cavity of said body, said flange defining a substantially planar surface around the inlet end of said conduit and also cooperating with said body to define a passageway therebetween, the planar surface of said flange being located inside the body cavity and adjacent to the second opening of said body; and a sealing means located outside of the internal cavity of the body and adjacent to the periphery of the second opening such that when the sealing means is in contact with and urged against the surface of the object, the body and flange cooperate with said surface to form a chamber that is in communication with the first opening of said body through said passageway and said internal cavity, and wherein said chamber is also in communication with the outlet end of said conduit through the inlet end of said conduit.

10. The apparatus of claim 9 wherein said body comprises a tube having a radially extending foot portion with said second opening of the body being included in the foot portion, and wherein said sealing means is in contact with said foot portion adjacent to the periphery of said second opening.

11. The apparatus of claim 6 or claim 10 and further comprising:

a plate member having a cut-out portion that is dimensioned to received said body, said plate member cooperating with the foot of said body at times when said body is received in said cut-out portion and said sealing means is in contact with said surface while said plate member is urged toward the object to provide a means for maintaining said sealing means in contact with the surface of the object.

12. The apparatus of claim 9 or claim 10 wherein the perimeter of the first opening of said body substantially defines a first plane and the perimeter of the second opening of said body substantially defines a second plane, where said second plane is disposed in substantially non-parallel relationship with respect to the first plane.

13. The apparatus of claim 9 or claim 10 wherein the perimeter of the first opening of said body substantially defines a first plane and the perimeter of the second opening of said body substantially defines a second plane, where said second plane is disposed in substantially orthogonal relationship with respect to the first plane.

* * * * *